United States Patent [19]

Engel et al.

[11] 4,259,336
[45] Mar. 31, 1981

[54] 4-HYDROXY-2H-[1]-BENZOTHIENO [2,3-E]-1,2-THIAZINE-3-CARBOXAMIDE-1,1-DIOXIDES AND SALTS THEREOF

[75] Inventors: Wolfhard Engel; Günter Trummlitz; Ernst Seeger; Walter Haarmann; Günther Engelhardt; Rainer Zimmermann, all of Biberach, Fed. Rep. of Germany

[73] Assignee: Boehringer Ingelheim GmbH, Ingelheim am Rhein, Fed. Rep. of Germany

[21] Appl. No.: 86,743

[22] Filed: Oct. 22, 1979

Related U.S. Application Data

[63] Continuation-in-part of Ser. No. 68,673, Aug. 22, 1979, abandoned.

[30] Foreign Application Priority Data

Sep. 2, 1978 [DE] Fed. Rep. of Germany ....... 2838377

[51] Int. Cl.³ .................. C07D 513/04; A61K 31/38
[52] U.S. Cl. ...................................... 424/246; 544/33
[58] Field of Search ........................... 544/33; 424/246

[56] References Cited

U.S. PATENT DOCUMENTS 4,137,313  1/1979  Trummlitz et al. .................... 544/33

*Primary Examiner*—John M. Ford

*Attorney, Agent, or Firm*—Hammond & Littell, Weissenberger & Muserlian

[57] ABSTRACT

Compounds of the formula

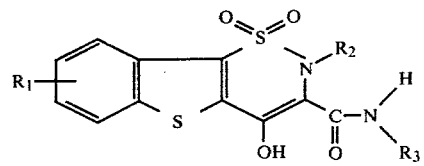

wherein $R_1$ is hydrogen, halogen or alkyl of 1 to 3 carbon atoms;
$R_2$ is hydrogen or alkyl of 1 to 3 carbon atoms; and
$R_3$ is aromatic hydrocarbyl of 6 to 10 carbon atoms or an aromatic heterocycle of 2 to 9 carbon atoms and 1 to 2 nitrogen atoms and/or an oxygen or a sulfur atom, where each of said aromatic substituents may in turn be substituted with one or two alkyls of 1 to 6 carbon atoms, halogen, hydroxyl, trifluoromethyl, halophenyl or alkoxy of 1 to 3 carbon atoms;

and non-toxic, pharmacologically acceptable salts thereof formed with inorganic or organic bases; the compounds as well as their salts are useful as analgesics, antipyretics, antithrombotic and antiphlogistics.

9 Claims, No Drawings

4-HYDROXY-2H-[1]-BENZOTHIENO[2,3-e]-1,2-THIAZINE-3-CARBOXAMIDE-1,1-DIOXIDES AND SALTS THEREOF

This is a continuation-in-part of copending application Ser. No. 068,673, filed Aug. 22, 1979, now abandoned.

This invention relates to novel 4-hydroxy-2H-[1]-benzothieno[2,3-e]-1,2-thiazine-3-carboxamide-1,1-dioxides and non-toxic salts thereof formed with inorganic or organic bases, to methods of preparing these compounds, to pharmaceutical composition containing them as active ingredients, and to methods of using the same as antiphlogistics and antithrombotics.

More particularly, the present invention relates to a novel class of compounds represented by the formula

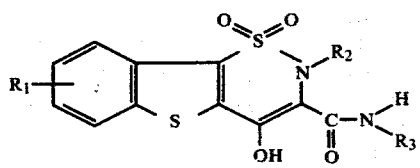

wherein $R_1$ is hydrogen, halogen or alkyl of 1 to 3 carbon atoms;

$R_2$ is hydrogen or alkyl of 1 to 3 carbon atoms; and $R_3$ is aromatic hydrocarbyl of 6 to 10 carbon atoms or an aromatic heterocycle of 2 to 9 carbon atoms and 1 to 2 nitrogen atoms and/or an oxygen or a sulfur atom, where each of said aromatic substituents may in turn be substituted with one or two alkyls of 1 to 6 carbon atoms, halogen, hydroxyl, trifluoromethyl, halophenyl or alkoxy of 1 to 3 carbon atoms;

and non-toxic, pharmacologically acceptable salts thereof formed with inorganic or organic bases.

Illustrative examples of the aromatic hydrocarbyl and aromatic heterocyclic radicals defined by $R_3$ above are the following: Phenyl, naphthyl, pyridyl, pyrimidyl, pyrazinyl, pyridazinyl, oxazolyl, isoxazolyl, thiazolyl, isothiazolyl, benzothiazolyl, 4,5,6,7-tetrahydro-benzothiazolyl, cyclopentathiazolyl, and 1,3,4-thiadiazolyl.

A preferred sub-genus under the genus defined by formula I is constituted by those compounds wherein $R_1$ is hydrogen, halogen or alkyl of 1 to 3 carbon atoms;

$R_2$ is hydrogen or alkyl of 1 to 3 carbon atoms; and $R_3$ is phenyl, naphthyl, pyridyl, pyrimidyl, pyrazinyl, pyridazinyl, oxazolyl, isoxazolyl, thiazolyl, isothiazolyl, benzothiazolyl, cyclopentathiazolyl or 1,3,4-thiadiazolyl, where each of these may be substituted with one or two alkyls of 1 to 6 carbon atoms, halogen, hydroxyl, trifluoromethyl, halophenyl or alkoxy of 1 to 3 carbon atoms;

and non-toxic, pharmacologically acceptable salts thereof formed with inorganic or organic bases.

An especially preferred sub-genus thereunder is constituted by those compounds of the formula I wherein $R_1$ is hydrogen, chlorine or methyl;

$R_2$ is methyl; and $R_3$ is phenyl, chloro-phenyl, pyridyl, chloropyridyl, hydroxy-pyridyl, methyl-pyridyl, thiazolyl, mono- or di-(alkyl of 1 to 4 carbon atoms)-thiazolyl, chloro-thiazolyl, trifluoromethyl-thiazolyl, chlorophenyl-thiazolyl, benzothiazolyl, 5,6-dimethyl-benzothiazolyl, 4,5,6,7-tetrahydro-benzothiazolyl, 5,6-dihydro-4H-cyclopentathiazolyl, 5-methyl-isoxazolyl, pyrimidyl or pyrazinyl;

and non-toxic, pharmacologically acceptable salts thereof formed with inorganic or organic bases.

The compounds embraced by formula I may be prepared by reacting a 4-hydroxy-2H-[1]-benzothieno[2,3-e]-1,2-thiazine-3-carboxylic acid derivative of the formula

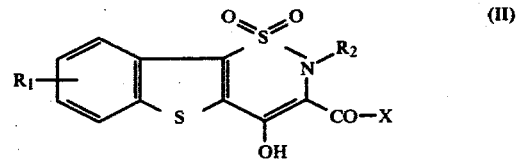

wherein $R_1$ and $R_2$ have the same meanings as in formula I; and

X is a nucleophilic exchangeable substituent, such as alkoxy of 1 to 6 carbon atoms or aralkoxy of 7 to 10 carbon atoms, with an amine of the formula

wherein $R_3$ has the same meanings as in formula I.

The reaction is advantageously carried out in a suitable inert organic solvent, for example, in an aromatic hydrocarbon such as benzene, toluene, xylene, chlorobenzene, o-dichlorobenzene or tetrahydronaphthalene, or in a dipolar aprotic solvent such as dimethylformamide, dimethylacetamide, hexamethylphosphoric acid triamide, or dimethylsulfoxide, or in an ether such as dimethoxyethane, diethyleneglycol-dimethylether or diphenylether, or in an excess of the amine of the formula III at temperatures between 60° and 200° C., preferably, however, at the boiling point of the reaction mixture. However, the reaction can also be carried out in the absence of a solvent.

The reaction is especially advantageously carried out in the presence of toluene or xylene at the boiling point of these solvents, whereby the alcohol HX released by the reaction is simultaneously removed by azeotropic distillation, or by using a Soxhlet-extractor equipped with a molecular sieve.

The compounds embraced by formula I form non-toxic, pharmacologically acceptable salts with inorganic or organic bases. Examples of such salts are those formed with alkali metal alcoholates, such as sodium ethylate; alkali metal hydroxides, such as sodium hydroxide or potassium hydroxide; alkaline earth metal hydroxides, such as calcium hydroxide; tetraalkyl ammonium hydroxides, such as tetraethyl ammonium hydroxide; or alkylamines, such as methylamine or cyclohexylamine.

The starting compounds of the formula II may be prepared pursuant to the following schematic reaction sequence:

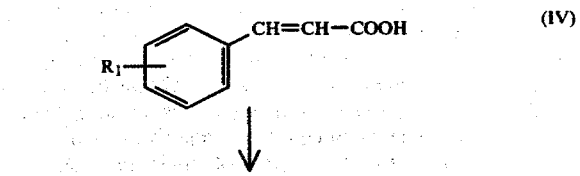

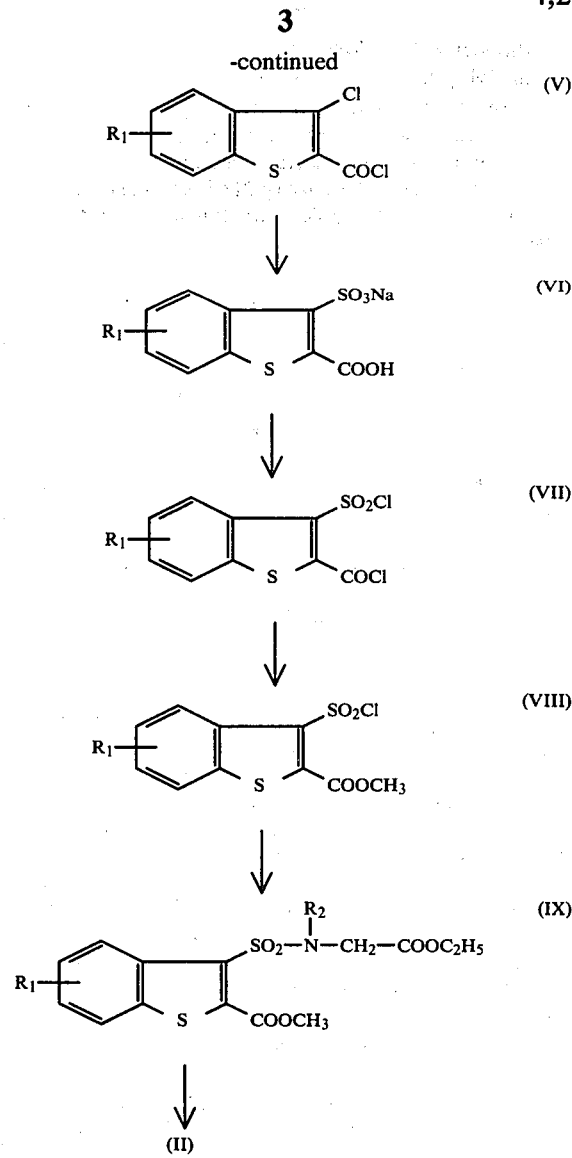

where $R_1$ and $R_2$ have the same meanings as in formula I. For this purpose a cinnamic acid of the formula IV is converted at elevated temperatures into a 3-chloro-benzo[b]thiophene-2-carboxylic acid chloride of the formula V [see W. B. Wright et al. in J. Het. Chem. 8, 711 (1971); T. Higa et al. in J. Org. Chem. 40, 3037 (1975); and ibid. 41, 3399 (1976)] by means of thionylchloride in pyridine, which is subsequently hydrolized in alkaline solution. The thus obtained alkali metal salt of the 3-chlorobenzo-[b]thiophene-2-carboxylic acid is reacted in aqueous solution with sodium hydrogen sulfite in the presence of a copper-(I)-halide in an autoclave at temperatures between 135° and 150° C. By acidifying with concentrated hydrochloric acid and addition of sodium chloride, a compound of the formula VI is obtained which, after drying, is converted into the corresponding acid chloride of the formula VII. This conversion is effected by means of at least 2 mols of phosphorus pentachloride in phosphorus oxide trichloride at temperatures between 30° C. and the boiling point of the mixture. The acid chloride of the formula VII thus obtained is subsequently converted into the corresponding ester of the formula VIII by means of methanolysis, which is then converted into a compound of the formula IX by reaction with a corresponding glycine ester. The conversion of the compound of the formula IX thus obtained into a starting compound of the formula II is carried out by reaction with an alcoholate of an alcohol of the formula $$H—X \qquad (X)$$

wherein X has the meanings previously defined, in the presence of a corresponding anhydrous alcohol at temperatures between 10° and 80° C.

The starting compounds of the formula III are to a large extent known from the literature. For example, 2-amino-4,5,6,7-tetrahydro-benzothiazole, 2-amino-4-(1,1-dimethylethyl)-thiazole and 2-amino-4-(4-chlorophenyl)thiazole are obtained according to L. C. King et al., J. Amer. Chem. Soc. 72, 3722 (1950), by reaction of a corresponding ketone with thiourea and iodine; 4-trifluoromethyl-2-thiazolamines obtained by reaction of 1-bromo-3,3,3-trifluoro-acetone with thiourea [see J. B. Dickey et al., J. Org. Chem. 20, 409, 505 ff. (1955)]; and 5-alkyl-2-thiazolamine are obtained by chlorination of a suitable primary alcohol at 0° to 5° C. and subsequent reaction with thiourea [see M. V. Shirsat, C. A. 54, 14230e (1960)].

The following examples illustrate the present invention and will enable others skilled in the art to understant it more completely. It should be understood, however, that the invention is not limited solely to the particular examples given below.

EXAMPLE 1

4-Hydroxy-2-methyl-N-(2-thiazolyl)-2H-[1]benzothieno[2,3-e]-1,2-thiazine-3-carboxamide-1,1-dioxide 25.0 gm (0.0768 mol) of methyl 4-hydroxy-2-methyl-2H-[1]benzothieno-[2,3-e]-1,2-thiazine-3-carboxylate-1,1-dioxide and 10.0 gm (0.12 mol) of 2-thiazolamine were refluxed for 16 hours in 300 cc of anhydrous xylene in an atmosphere of nitrogen. The released methanol was removed by means of 4 Å-molecular sieve filled in a Soxhlet apparatus. After cooling and standing for several hours, the reaction product was filtered off. After recrystallization from a mixture of dimethylformamide and 1,2-dichloroethane 19.9 gm (66% of theory) of light-yellow 4-hydroxy-2-methyl-N-(2-thiazolyl)-2H-[1]benzothieno[2,3-e]-1,2-thiazine-3-carboxamide-1,1-dioxide were obtained.

M.p. 252°–253° C. (decomp.).

$C_{15}H_{11}N_3O_4S_3$ (393.47): Calc. C-45.79%; H-2.82%; N-10.68%; S-24.45%; Found: C-45.80%; H-2.85%; N-10.66%; S-24.50%

IR(KBr): N—H 3300, C=O 1630, amide-II 1540, $SO_2$ 1340, 1150/cm

UV(ethanol): $\lambda_{max}$ 407 and 378 nm, shoulder at 260 nm; after addition of KOH; $\lambda_{max}$ 285 and 414 nm.

1H-NMR (d$_6$-DMSO): δ 8.4–8.0 (2H-m, ar. H); 7.8–7.4 (2H-m, ar.H); 7.61 (1H-d, J=4.4 Hz, 4'-H); 7.26 (1H-d, J=4.4 Hz, 5'-H); 3.03 (3H-s, 2-CH$_3$) and 2 exchangeable protons.

The starting compound was obtained by the following reaction sequence:

(a) Sodium 2-carboxy-benzo[b]thiophene-3-sulfonate 74.0 gm (0.32 mol) of 3-chloro-benzo[b]thiophene-2-carboxylic acid chloride (m.p. 112°–113° C.) were stirred with a solution of 25.6 gm (0.64 mol) of sodium hydroxide in 250 cc of water for 12 hours while keeping the reaction temperature at 50° C. Thereafter 66.6 gm (0.64 mol) of solid sodium hydrogen sulfite were added to the neutral-reacting solution. The reaction mixture was made slightly alkaline by addition of a 40% sodium hydroxide solution and heated for 16 hours to 143° C. in an autoclave after addition of 3.0 gm (0.03 mol) of copper(I)-chloride. After cooling, the mixture was adjusted to pH 4 by adding hydrochloric acid, filtered and extracted once with 200 cc of ethyl acetate to remove the residual unreacted starting material. After further acidification to pH 1 and by addition of 60 gm of sodium chloride a colorless precipitate was obtained from the aqueous phase, which was suction-filtered off, washed with 30 cc of saturated aqueous sodium chloride solution and suction-filtered. The reaction product was dissolved in warm methanol and separated from the insoluble excess sodium chloride. The solvent was evaporated in vacuo, and the residue was dried by azeotropic distillation with 50 cc of toluene. 43 gm (48% of theory) of colorless crude sodium 2-carboxy-benzo[b]-thiophene-3-sulfonate were obtained, which were further processed without further purification.

(b) 2-Chlorocarbonyl-benzo[b]thiophene-3-sulfonic acid chloride 44.0 gm (0.157 mol) of the above 2-carboxy-benzo[b]-thiophene-3-sulfonic acid mono sodium salt were suspended in 200 cc of phosphorus oxychloride and admixed with 65.4 gm (0.314 mol) of phosphorus-(V)-chloride. To complete the reaction which was exothermic in the beginning accompanied by evolution of hydrogen chloride, the reaction mixture was heated to 100° C. for 2 hours, cooled and the inorganic salts were filtered off. After evaporation in vacuo, the residue was taken up in 300 cc of dry chloroform, the solution was filtered and again evaporated. The oily residue, consisting of 27 gm (58% of theory) of raw 2-chlorocarbonyl-benzo[b]thiophene-3-sulfonic acid chloride, crystallized upon cooling (m.p. 45°–47° C.) and was used without further purification in the next step.

(c) 2-Methoxycarbonyl-benzo[b]thiophene-3-sulfonic acid chloride 168.0 gm (0.569 mol) of 2-chlorocarbonyl-benzo[b]-thiophene-3-sulfonic acid chloride were dissolved in 1 liter of anhydrous chloroform, and the solution was admixed with 27.5 gm (0.858 mol) of dry methanol and refluxed for 3 hours. The reaction mixture was evaporated in vacuo, and the residue was recrystallized twice from a little methanol, yielding 88.5 gm (53.5% of theory) of colorless 2-methoxycarbonyl-benzo[b]-thiophene-3-sulfonic acid chloride. M.p.: 100°–101° C.

$C_{10}H_7ClO_4S_2$ (290.75): Calc.: C-41.31%; H-2.43%; Cl-12.19%; S-22.06% Found: C-41.35%; H-2.53%; Cl-12.55%; S-22.90%

IR ($CH_2Cl_2$): C=O 1740, $SO_2$ 1175, 1380/cm

UV(ethanol): $\lambda_{max}$ 254, 305 nm; after addition of KOH: $\lambda_{max}$ 280, shoulder at 240 nm.

1H-NMR (CDCl₃): δ 8.6–8.2 (1H-m, ar. H); 8.1–7.8 (1H-m, ar.H), 7.8–7.4 (2H-m, ar.H); 4.06 (3H-s, ester-CH₃).

(d) Methyl 3-{[ethoxycarbonyl-methyl)methylamino]sulfonyl}benzo[b]thiophene-2-carboxylate While cooling on an ice water bath, first 182 gm (1.799 mol) of triethylamine and then a solution of 252.0 gm (0.867 mol) of 2-methoxycarbonyl-benzo[b]thiophene-3-sulfonic acid chloride in a mixture of 1 liter of diethyl ether and 1 liter of tetrahydrofuran were added dropwise to a solution of 138.0 gm (0.898 mol) of sarcosine ethyl ester hydrochloride in 300 cc of methanol. After stirring for 30 minutes at room temperature and refluxing for further 30 minutes, the reaction mixture was evaporated in vacuo. The residue was taken up in 1 liter of chloroform, the resulting solution was washed successively with 200 cc of water, aqueous 5% hydrochloric acid and again with water, dried and evaporated over sodium sulfate. The residue was recrystallized twice from ethanol, yielding 286 gm (89% of theory) of colorless methyl 3-}[(ethoxycarbonylmethyl)-methylamino]sulfonyl}benzo[b]thiophene-2-carboxylate.

M.p.: 119°–120° C.

$C_{15}H_{17}NO_6S_2$ (371.44): Calc. C-48.51%; H-4.61%; N-3.77%; S-17.26%; Found: C-48.45%; H-4.65%; N-3.95%; S-17.50%

IR ($CH_2Cl_2$): C=O 1740, $SO_2$ 1150, 1350/cm

UV (ethanol): $\lambda_{max}$ 290, shoulder at 245 nm

1H-NMR (CDCl₃): δ 8.6–8.2 (1H-m, ar. H); 8.0–7.7 (1H-m, ar. H); 77.7–7.3 (2H-m, ar.H); 4.22 (2H-s, N—CH₂—C); 3.99 (3H-s, OCH₃); 4.02 (2H-q; J=7.2 Hz, —O—CH₂C), 3.11 (3H-s; NCH₃); 1.10 (3H-t, J=7.2 Hz, —O—C—CH₃).

(e) Methyl 4-hydroxy-2-methyl-2H-[1]benzothieno[2,3-e]-1,2-thiazine-3-carboxylate-1,1-dioxide 42.0 gm (0.78 mol) of solid sodium methylate were added in an inert gas atmosphere to a suspension of 286 gm (0.77 mol) of methyl 3-{[(ethoxycarbonylmethyl)-methylamino]sulfonyl}-benzo[b]thiophene-2-carboxylate in 1000 cc of anhydrous methanol. The mixture was stirred for 30 minutes at room temperature and then refluxed for 1 hour. The solvent was distilled off, and the residue was stirred into 500 ml of ice-cold 2 N hydrochloric acid. The precipitated product was filtered off, taken up in 400 cc of chloroform, and the solution was dried over sodium sulfate and evaporated in vacuo. After recrystallizing the residue twice from 100 cc each of methanol, 116 gm (46% of theory) of light-yellow crystals were obtained.

M.p. 177°–178° C.

$C_{13}H_{11}NO_5S_2$ (325.36): Calc. C-47.99%; H-3.41%; N-4.30%; S-19.71%; Found: C-48.45%; H-3.55%; N-4.68%; S-19.85%

IR ($CH_2Cl_2$): OH broad, associated, C=O 1660, $SO_2$ 1160, 1350/cm

UV (ethanol): $\lambda_{max}$ 345, shoulder at 255 nm; after addition of KOH: $\lambda_{max}$ 235, 290, 385, 405 nm 1H-NMR (CDCl₃): δ 11.84 (1H-s, exchangeable H); 8.5–8.1 (1H-m, ar. H); 8.1–7.8 (1H-m, ar.H); 7.7–7.4 (2H-m, ar.H). 3.99 (3H-s, OCH₃); 3.10 (3H-s, N—CH₃).

EXAMPLE 2

4-Hydroxy-2-methyl-N-(2-pyridyl)-2H-[1]benzothieno[2,3-e]-1,2-thiazine-3-carboxamide-1,1-dioxide Prepared analogous to Example 1 from methyl 4-hydroxy-2-methyl-2H-[1]-benzothieno[2,3-e]-1,2-thiazine-3-carboxylate-1,1-dioxide and 2-amino-pyridine with a yield of 52% of theory.

M.p.: 224°–225° C. (decomp.) after recrystallization from ethylene chloride.

$C_{17}H_{13}N_3O_4S_2$ (387.44): Calc.: C-52.70%; H-3.38%; N-10.85%; S-16.55%; Found: C-52.30%; H-3.41%; N-11.0%; S-16.70%

IR ($CH_2Cl_2$): OH, NH broad associated, C=O 1630-1640, $SO_2$ 1150, 1340/cm

UV (ethanol): $\lambda_{max}$ 367, 403 nm; after addition of KOH: $\lambda_{max}$ 413 nm 1H-NMR ($d_6$-DMSO): δ 14.41 (1H-s, exchangeable H); 8.5-7.0 (8H-m, ar.H); 5.0-3.8 (1H-m, broad, exchangeable H); 2.98 (3H—S, N—$CH_3$).

EXAMPLE 3

4-Hydroxy-2-methyl-N-(6-methyl-2-pyridyl)-2H-[1]benzothieno-[2,3-e]-1,2-thiazine-3-carboxamide-1,1-dioxide Prepared analogous to Example 1 from methyl 4-hydroxy-2-methyl-2H-[1]-benzothieno[2,3-e]-1,2-thiazine-3-carboxylate-1,1-dioxide and 2-amino-6-methyl-pyridine with a yield of 33% of theory.

M.p.: 233°-234° C. (decomp.) after recrystallization from dimethylformamide.

$C_{18}H_{15}N_3O_4S_2$ (401.47): Calc.: C-53.85%; H-3.77%; N-10.47%; S-15.97%; Found: C-53.70%; H-3.95%; N-10.25%; S-15.80%

EXAMPLE 4

4-Hydroxy-2-methyl-N-(4-methyl-2-thiazolyl)-2H-[1]benzothieno[2,3-e]-1,2-thiazine-3-carboxamide-1,1-dioxide Prepared analogous to Example 1 from methyl 4-hydroxy-2-methyl-2H-[1]benzothieno[2,3-e]-1,2-thiazine-3-carboxylate-1,1-dioxide and 2-amino-4-methyl-thiazole with a yield of 66% of theory.

M.p.: 243°-244° C. (decomp.) after recrystallization from ethylene chloride.

$C_{16}H_{13}N_3O_4S_3$ (407.49): Calc.: C-47.16%; H-3.22%; N-10.30%; S-23.61%; FOund: C-47.00%; H-3.30%; N-10.37%; S-23.70

EXAMPLE 5

N-(2-Benzothiazolyl)-4-hydroxy-2-methyl-2H-[1]benzothieno-[2,3-e]-1,2-thiazine-3-carboxamide-1,1-dioxide Prepared analogous to Example 1 from ethyl 4-hydroxy-2-methyl-2H-[1]-benzothieno[2,3-e]-1,2-thiazine-3-carboxylate-1,1-dioxide and 2-amino-benzothiazole with a yield of 70% of theory.

M.p.: 255°-256° C. (decomp.) after recrystallization from dimethylformamide.

$C_{19}H_{13}N_3O_4S_3$ (443.52): Calc.: C-51.45%; H-2.95%; N-9.47%; S-21.69%; Found: C-51.50%; H-3.00%; N-9.42%; S-21.68%

EXAMPLE 6

N-(4-Chloro-phenyl)-4-hydroxy-2-methyl-2H-[1]benzothieno-[2,3-e]-1,2-thiazine-3-carboxamide-1,1-dioxide Prepared analogous to Example 1 from benzyl 4-hydroxy-2-methyl-2H-[1]-benzothieno[2,3-e]-1,2-thiazine-3-carboxylate-1,1-dioxide and 4-chloro-aniline with a yield of 52% of theory.

M.p.: 251°-252° C. (decomp.) after recrystallization from ethyleneglycol monomethyl ether.

$C_{18}H_{13}ClN_2O_4S_2$ (420.9): Calc.: C-51.37%; H-3.11%; N-6.66%; Cl-8.42%; S-15.24%; Found: C-51.40%; H-3.18%; N-6.30%; Cl-8.55%; S-15.55%

EXAMPLE 7

4-Hydroxy-2-methyl-N-phenyl-2H-[1]-benzothieno[2,3-e]-1,2-thiazine-3-carboxamide-1,1-dioxide Prepared analogous to Example 1 from methyl 4-hydroxy-2-methyl-2H-[1]benzothieno[2,3-e]-1,2-thiazine-3-carboxylate-1,1-dioxide and aniline with a yield of 60% of theory.

M.p.: 256°-257° C. (decomp.) after recrystallization from ethyleneglycol monomethyl ether.

$C_{18}H_{14}N_2O_4S_2$ (386.45): Calc.: C-55.44%; H-3.65%; N-7.25%; S-16.59%; Found: C-55.90%; H-3.68%; N-7.34%; S-16.20%

EXAMPLE 8

4-Hydroxy-2-methyl-N-(5-methyl-3-ixoxazolyl)-2H-[1]benzothieno[2,3-e]-1,2-thiazine-3-carboxamide-1,1-dioxide Prepared analogous to Example 1 from methyl 4-hydroxy-2-methyl-2H-[1]benzothieno[2,3-e]-1,2-thiazine-3-carboxylate-1,1-dioxide and 5-methyl-3-isoxazolamine with a yield of 29% of theory.

M.p.: 245°-246° C. (decomp.) after two recrystallizations from tetrahydrofuran.

$C_{16}H_{13}N_3O_5S_2$ (391.43): Calc.: C-49.10%; H-3.35%; N-10.74%; S-16.38%; Found: C-49.20%; H-3.56%; N-10.75%; S-16.78%

EXAMPLE 9

4-Hydroxy-2-methyl-N-(4-methyl-2-pyridyl)-2H-[1]benzothieno-[2,3-e]-1,2-thiazine-3-carboxamide-1,1-dioxide Prepared analogous to Example 1 from methyl 4-hydroxy-2-methyl-2H-[1]benzothieno[2,3-e]-1,2-thiazine-3-carboxylate-1,1-dioxide and 4-methyl-2-amino-pyridine with a yield of 31% of theory.

M.p.: 230°-231° C. (decomp.) after recrystallization from 1,2-dichloro ethane.

$C_{18}H_{15}N_3O_4S_2$ (401.47): Calc.: C-53.85%; H-3.77%; N-10.47%; S-15.97%; Found: C-53.50%; H-3.82%; N-10.10%; S-15.50%

IR (KBr): OH, NH broad associated, C=O— 1640-1650, $SO_2$ 1150, 1330/cm

UV (ethanol): shoulder at about 260, $\lambda_{max}$ 390; after addition of KOH: $\lambda_{max}$ 266, 295, 398 nm 1H-NMR ($d_6$-DMSO): δ 14.52 (1H-s, exchangeable H); 8.3-8.0 (3H-m, ar. H); 7.8-7.4(3H-m, ar. H) 7.3-7.1 (1H-m, ar. H); 4.2-3.2 (1H-s, broad, exchangeable H); 2.94 (3H-s; N—$CH_3$); 2.48 (3H-s, ≧C—$CH_3$).

EXAMPLE 10

4-Hydroxy-2-methyl-N-(5-methyl-2-thiazolyl)-2H-[1]benzothieno[2,3-e]-1,2-thiazine-3-carboxamide-1,1-dioxide Prepared analogous to Example 1 from methyl 4-hydroxy-2-methyl-2H-[1]benzothieno[2,3-e]-1,2-thiazine-3-carboxylate-1,1-dioxide and 5-methyl-2-thiazolamine with a yield of 46% of theory.

M.p.: 247°-248° C. after recrystallization from dimethylformamide.

$C_{16}H_{13}N_3O_4S_3$ (407.49): Calc.: C-47.16; H-3.27%; N-10.30%; S-23.61%; Found: C-47.25%; H-3.30%; N-10.24%; S-23.50%

EXAMPLE 11

N-(4,5-Dimethyl-2-thiazolyl)-4-hydroxy-2-methyl-2H-[1]benzothieno[2,3-e]-1,2-thiazine-3-carboxamide-1,1-dioxide Prepared analogous to Example 1 from methyl 4-hydroxy-2-methyl-2H-[1]-benzothieno[2,3-e]-1,2-thiazine-3-carboxylate-1,1-dioxide and 4,5-dimethyl-2-thiazolamine with a yield of 56% of theory.

M.p.: 243°–244° C. (decomp.) after recrystallization from 1,2-dichloro ethane.

$C_{17}H_{15}N_3O_4S_3$ (421.52):
Calc.: C-48.44%; H-3.59%; N-9.97%; S-22.82%; Found: C-47.70%; H-3.65%; N-9.75%; S-22.18%.

EXAMPLE 12

N-(5-Ethyl-2-thiazolyl)-4-hydroxy-2-methyl-2H-[1]benzothieno[2,3-e]-1,2-thiazine-3-carboxyamide-1,1-dioxide Prepared analogous to Example 1 from ethyl 4-hydroxy-2-methyl-2H-[1] benzothieno [2,3-3]-1,2-thiazine-3-carboxylate-1,1-dioxide and 5-ethyl-2-thiazolamine with a yield of 38% of theory.

M.p.: 219°–220° C. after recrystallization from 1,2-dichloroethane.

$C_{17}H_{15}N_3O_4S_3$ (421.52): Calc.: C-48.44%; H-3.59%; N-9.97%; S-22.82%; Found: C-48.20%; H-3.75%; N-9.90%; S-22.60%.

EXAMPLE 13

4-Hydroxy-2-methyl-N-(5-propyl-2-thiazolyl)-2H-[1]benzothieno [2,3-e]-1,2-thiazine-3-carboxamide-1,1-dioxide Prepared analogous to Example 1 from methyl 4-hydroxy-2-methyl-2H-[1] benzothieno [2,3-e]-1,2-thiazine-3-carboxylate-1,1-dioxide and 5-propyl-2-thiazolamine with a yield of 37% of theory.

M.p.: 217°–218° C. (decomp. after recrystalization from 1,2-dichloro ethane.

$C_{18}H_{17}N_3O_4S_3$ (435.55): Calc.: C-49.64%; H-3.93%; N-9.65%; S-22.09%; Found: C-49.70%; H-4.02%; N-9.61%; S-22.02%

EXAMPLE 14

N-[4-(1,1-Dimethylethyl)-2-thiazolyl]-4-hydroxy-2methyl-2H-[1] benzothieno [2,3-e]-1,2-thiazine-3-carboxamide-1,1-dioxide Prepared analogous to Example 1 from methyl 4-hydroxy-2-methyl-2H-[1] benzothieno [2,3-e]-1,2-thiazine-3-carboxylate-1,1-dioxide and 4-(1,1-dimethylethyl)-2-thiazolamine with a yield of 33% of theory.

M.p.: 214°–215° C. (decomp.) after recrystallization from 1,2-dichloro ethane.

$C_{19}H_{19}N_3O_4S_3$ (449.57): Calc.: C-50.76%; H-4.26%; N-9.35%; S-21.40%; Found: C-51.10%; H-4.38%; N-9.26%; S-21.60%

EXAMPLE 15

N-(5-Chloro-2-thiazolyl)-4-hydroxy-2-methyl-2H-[1] benzothieno [2,3-e]-1,2-thiazine-3-carboxamide-1,1-dioxide Prepared analogous to Example 1 from methyl 4-hydroxy-2-methyl-2H-[1] benzothieno [2,3-e]-1,2-thiazine-3-carboxylate-1,1-dioxide and 5-chloro-2-thiazolamine with a yield of 34% of theory.

M.p.: 252°–253° C. (decomp.) after recrystallization from a mixture of dimethylformamide and methanol.

$C_{15}H_{10}ClN_3O_4S_3$ (427.91): Calc.: C-42.10%; H-2.36%; N-9.82%; Cl-8.29%; S-22.48%; Found: C-42.15%; H-2.45%; N-9.70%; Cl-8.63%; S-22.40%

EXAMPLE 16

N-[4-(4-Chlorophenyl)-2-thiazolyl]-4-hydroxy-2-methyl-2H-[1] benzothieno [2,3-e]-1,2-thiazine-3-carboxamide-1,1-dioxide Prepared analogous to Example 1 from ethyl 4-hydroxy-2-methyl-2H-[1]-benzothieno [2,3-e]-1,2-thiazine-3-carboxylate-1,1-dioxide and 4-(4-chlorphenyl)-2-thiazolamine with a yield of 40% of theory.

M.p.: 260°–261° C. (decomp.) after recrystallization from 1,2-dichloro ethane.

$C_{21}H_{14}ClN_3O_4S_3$ (504.0): Calc.: C-50.05%; H-2.80%; N-8.34%; Cl-7.03%; S-19.09%; Found: C-50.00%; H-2.95%; N-8.21%; Cl-7.21%; S-18.72%

EXAMPLE 17

4-Hydroxy-2-methyl-N-(4,5,6,7-tetrahydro-2-benzothiazolyl)-2H-[1] benzothieno [2,3-e]-1,2-thiazine-3-carboxamide-1,1-dioxide Prepared analogous to Example 1 from propyl 4-hydroxy-2-methyl-2H-[1] benzothieno [2,3-e]-1,2-thiazine-3-carboxylate-1,1-dioxide and 2-amino-4,5,6,7-tetrahydrobenzothiazole with a yield of 58% of theory.

M.p.: 241°–242° C. (decomp.) after recrystallization from dimethylformamide.

$C_{19}H_{17}N_3O_4S_3$ (447.56): Calc.: C-50.99%; H-3.83%; N-9.39%; S-21.49%; Found: C-51.00%; H-4.08%; N-9.39%; S-21.35%

EXAMPLE 18

N-(5,6-Dihydro-4H-cyclopentathiazole-2-yl)-4-hydroxy-2-methyl-2H-[1] benzothieno [2,3-e]-1,2-thiazine-3-carboxamide-1,1-dioxide Prepared analogous to Example 1 from methyl 4-hydroxy-2-methyl-2H-[1] benzothieno [2,3-e]-1,2-thiazine-3-carboxylate-1,1-dioxide and 5,6-dihydro-4H-cyclopentathiazole-2-amine with a yield of 57% of theory.

M.p.: 258°–259° C. (decomp.) after recrystallization from dimethylformamide.

$C_{18}H_{15}N_3O_4S_3$ (433.53): Calc.: C-49.87%; H-3.49%; N-9.69%; S-22.19%; Found: C-49.30%; H-3.51%; N-9.69%; S-21.85%

EXAMPLE 19

N-(5,6-Dimethyl-2-benzothiazolyl)-4-hydroxy-2-methyl-2H-[1] benzothieno [2,3-e]-1,2-thiazine-3-carboxamide 1,1-dioxide Prepared analogous to Example 1 from benzyl 4-hydroxy-2-methyl-2H-[1] benzothieno [2,3-e]-1,2-thiazine-3-carboxylate-1,1-dioxide and 5,6-dimethyl-2-benzothiazolamine with a yield of 80% of theory.

M.p.: 267°–268° C. (decomp.) after recrystallization from dimethylformamide.

$C_{21}H_{17}N_3O_4S_3$ (471.58): Calc.: C-53.49%; H-3.63%; N-8.91%; S-20.40%; Found: C-53.20%; H-3.66%; N-9.18%; S-20.30%

EXAMPLE 20

4-Hydroxy-2-methyl-N-(5-methyl-1,3,4-thiadiazole-2-yl)-2H-[1] benzothieno [2,3-e]-1,2-thiazine-3-carboxamide-1,1-dioxide Prepared analogous to Example 1 from methyl 4-hydroxy-2-methyl-2H-[1] benzothieno [2,3-e]-1,2-thiazine-3-carboxylate-1,1-dioxide and 2-amino-5-methyl-1,3,4-thiadiazole with a yield of 65% of theory.

M.p.: 253°–254° C. (decomp.) after recrystallization from a mixture of dimethylformamide and methanol.

$C_{15}H_{12}N_4O_4S_3$ (408.48): Calc.: C-44.11%; H-2.96%; N-13.72%; S-23.55%; Found: C-44.30%; H-3.12%; N-13.50%; S-23.25%

EXAMPLE 21

N-(5-Chloro-2-pyridyl)-4-hydroxy-2-methyl-2H-[1] benzothieno [2,3-e]-1,2-thiazine-3-carboxamide-1,1-dioxide Prepared analogous to Example 1 from methyl 4-hydroxy-2-methyl-2H-[1] benzothieno [2,3-e]-1,2-thiazine-3-carboxylate-1,1-dioxide and 2-amino-5-chloro-pyridine with a yield of 60% of theory.

M.p.: 232°–233° C. (decomp.) after recrystallization from dimethylformamide.

$C_{17}H_{12}ClN_3O_4S_2$ (421.89): Calc.: C-48.40%; H-2.87%; N-9.96%; Cl-8.40%; S-15.20%; Found: C-48.30%; H-2.87%; N-9.88%; Cl-8.73%; S-15.02%

EXAMPLE 22

4-Hydroxy-2-methyl-N-(2-pyrimidinyl)-2H-[1] benzothieno [2,3-e]-1,2-thiazine-3-carboxamide-1,1-dioxide Prepared analogous to Example 1 from methyl 4-hydroxy-2-methyl-2H[1] benzothieno [2,3-e]-1,2-thiazine-3-carboxylate-1,1-dioxide and 2-amino-pyrimidine with a yield of 39% of theory.

M.p.: 225°–226° C. (decomp.) after recrystallization from dimethylformamide.

$C_{16}H_{12}N_4O_4S_2$ (388.43): Calc.: C-49.48%; H-3.11%; N-14.42%; S-16.51%; Found: C-49.20%; H-3.29%; N-14.30%; S-16.20%

EXAMPLE 23

4-Hydroxy-2-methyl-N-(pyrazinyl)-2H-[1] benzothieno [2,3-e]-1,2-thiazine-3-carboxamide-1,1-dioxide Prepared analogous to Example 1 from ethyl 4-hydroxy-2-methyl-2H-[1] benzothieno [2,3-e]-1,2-thiazine-3-carboxylate-1,1-dioxide and aminopyrazine with a yield of 52% of theory.

M.p.: 234°–235° C. (decomp.) after recrystallization from a mixture of dimethylformamide and methanol.

$C_{16}H_{12}N_4O_4S_2$ (388.43): Calc.: C-49.48%; H-3.11%; N-14.42%; S-16.51%; Found: C-49.60%; H-3.14%; N-14.27%; S-16.30%

EXAMPLE 24

4-Hydroxy-2-methyl-N-(4-trifluoromethyl-2-thiazolyl)-2H-[1] benzothieno [2,3-e]-1,2-thiazine-3-carboxyamide-1,1-dioxide Prepared analogous to Example 1 from methyl-4-hydroxy-2-methyl-2H-[1] benzothieno [2,3-e]-1,2-thiazine-3-carboxylate-1,1-dioxide and 4-trifluoromethyl-2-thiazolamine with a yield of 53% of theory.

M.p.: 225°–226° C. after recrystallization from 1,2-dichloroethane.

$C_{16}H_{10}F_3N_3O_4S_3$ (461.47): Calc.: C-41.65%; H-2.18%; N-9.11%; S-20.84%; Found: C-41.70%; H-2.41%; N-8.73%; S-21.25%

EXAMPLE 25

2,7-Dimethyl-4-hydroxy-N-(2-pyridyl)-2H-[1] benzothieno [2,3-e]-1,2-thiazine-3-carboxamide-1,1-dioxide Prepared analogous to Example 1 from methyl 2,7-dimethyl-4-hydroxy-2H-[1] benzothieno [2,3-e]-1,2-thiazine-3-carboxylate-1,1-dioxide and 2-amino-pyridine with a yield of 53% of theory.

M.p.: 219°–220° C. (decomp.) after recrystallization from 1,2-dichloro-ethane.

$C_{18}H_{15}N_3O_4S_2$ (401.47): Calc.: C-53.85%; H-3.77%; N-10.47%; S-15.97%; Found: C-53.70%; H-3.86%; N-10.40%; S-15.80%

IR (KBr.): OH, NH broad, associated, C=O 1640, $SO_2$ 1140, 1330/cm

UV (ethanol: shoulder at 260, $\lambda_{max}$ 370 nm; after addition of KOH: $\lambda_{max}$ 265, 299, 414 nm 1H-NMR ($d_6$-DMSO): δ 8.5–7.1 (7H-m, ar.H); 5.5–4.0 (1H-s, broad, exchangeable H); 3.00 (3H-s, N—CH₃); 2.52 (3H-s, ≧C—CH₃).

The starting compound was obtained by the following reaction sequence:

(a) Monosodium 2-carboxy-6-methyl-benzo[b] thiophene-3-sulfonate

Prepared analogous to Example 1(a) from 3-chloro-6-methyl-benzo[b] thiophene-2-carboxylic acid chloride (m.p.: 124.5°–126° C.) by hydrolysis with aqueous sodium hydroxide solution and subsequent reaction with sodium hydrogen sulfite in the presence of copper-(I)-chloride as a catalyst.

Yield: 67% of theory.

(b) 2-Chlorocarbonyl-6-methyl-benzo[b] thiophene-3-sulfonic acid chloride

Prepared analogous to Example 1(b) from monosodium 2-carboxy-6-methyl-benzo[b] thiophene-3-sulfonate and phosphorus-(V)-chloride in the presence of phosphorus oxide trichloride with a yield of 82% of theory. The product, which crystallized upon cooling, was used in the next step without further purification.

(c) 2-Methoxycarbonyl-6-methyl-benzo[b] thiophene-3-sulfonic acid chloride

Prepared analogous to Example 1(c) from 2-chlorocarbonyl-6-methyl-benzo[b] thiophene-3-sulfonic acid chloride and methanol in the presence of chloroform.

Yield: 40% of theory

M.p.: 115°–117° C. after recrystallization from a mixture of methanol and ethyl acetate.

$C_{11}H_9ClO_4S_2$ (304.78): Calc.: C-43.35%; H-2.98%; Cl-11.63%; S-21.04%; Found: C-43.50%; H-3.04%; Cl-11.60%; S-21.02%

IR($CH_2Cl_2$): C=O 1740/cm

UV (ethanol): $\lambda_{max}$ 260, 310 nm; after addition of KOH: $\lambda_{max}$ 250, 295 nm.

(d) Methyl 3-{[(ethoxycarbonyl-methyl)-methylamino]sulfonyl}-6-methyl-benzo[b] thiophene-2-carboxylate Prepared analogous to Example 1(d) from 2-methoxycarbonyl-6-methyl-benzo[b] thiophene-3-sulfonic acid chloride, sarcosine ethyl ether hydrochloride and triethylamine with a yield of 80% of theory. M.p.: 86°–87° C. after recrystallization from ethanol.

(e) Methyl 2,7-dimethyl-4-hydroxy-2H-[1] benzothieno [2,3-e]-1,2-thiazine-3-carboxylate-1,1-dioxide Prepared analogous to Example 1(e) from methyl 3-{[(ethoxy-carbonyl-methyl)methylamino]sulfonyl}-6-methyl-benzo[b]thiophene-2-carboxylate by reaction with sodium methylate in anhydrous methanol with a yield of 51% of theory.

M.p.: 212°–213° C. after recrystallization from methanol.

$C_{14}H_{13}NO_5S_2$ (339.39): Calc.: C-49.55%; H-3.86%; N-4.13%; S-18.90%; Found: C-49.70%; H-4.01%; N-4.14%; S-18.50%

IR (KBr.): OH 3370, C=O 1720, 1680; $SO_2$ 1155, 1340/cm

UV (ethanol): $\lambda_{max}$ 265, 352 nm; after addition of KOH: $\lambda_{max}$ 230, 295, 385, 408 nm 1H-NMR(CDCl$_3$/CD$_3$OD): δ 8.22 (1H-d, J=8.4 Hz, ar. H in 9-position); 7.85 (1H-s, ar.H in 6-position); 7.46 (1H-d, J=8.4 Hz, ar. H in 8-position); 4.41 (1H-s, exchangeable H); 4.02 (3H-s, OCH$_3$); 3.11 (3H-s; N—CH$_3$); 2.54 (3H-s, ≧C—CH$_3$).

EXAMPLE 26

2,7-Dimethyl-4-hydroxy-N-(2-thiazolyl)-2H-[1] benzothieno-2,3-e]-1,2-thiazine-3-carboxamide-1,1-dioxide Prepared analogous to Example 1 from methyl 2,7-dimethyl-4-hydroxy-2H-[1] benzothieno [2,3-e]-1,2-thiazine-3-carboxylate-1,1-dioxide and 2-amino-thiazole with a yield of 58% of theory.

M.p.: 248°–249° C. (decomp.) after recrystallization from dimethylformamide.

$C_{16}H_{13}N_3O_4S_3$ (407.49): Calc.: C-47.16%; H-3.22%; N-10.31%; S-23.61%; Found: C-47.45%; H-3.37%; N-10.21%; S-23.20

EXAMPLE 27

2,7-Dimethyl-4-hydroxy-N-(4-methyl-2-thiazolyl)-2H-[1] benzothieno [2,3-e]-1,2-thiazine-3-carboxamide-1,1-dioxide Prepared analogous to Example 1 from ethyl 2,7-dimethyl-4-hydroxy-2H-[1] benzothieno [2,3-e]-1,2-thiazine-3-carboxylate-1,1-dioxide and 2-amino-4-methyl-thiazole with a yield of 40% of theory.

M.p.: 245°–246° C. (decomp.) after recrystallization from 1,2-dichloro-ethane.

$C_{17}H_{15}N_3O_4S_3$ (421.52): Calc.: C-48.44%; H-3.59%; N-9.97%; S-22.82%; Found: C-48.50%; H-3.64%; N-10.07%; S-23.30%

EXAMPLE 28

2,7-Dimethyl-2-hydroxy-N-(5-methyl-2-thiazolyl)-2H-[1] benzothieno [2,3-e]-1,2-thiazine-3-carboxamide-1,1-dioxide Prepared analogous to Example 1 from methyl 2,7-dimethyl-4-hydroxy-2H-[1] benzothieno [2,3-e]-1,2-thiazine-3-carboxylate-1,1-dioxide and 2-amino-5-methyl-thiazole with a yield of 64% of theory.

M.p.: 251°–252° C. (decomp.) after recrystallization from dimethylformamide.

$C_{17}H_{15}N_3O_4S_3$ (421.52): Calc.: C-48.44%; H-3.59%; N-9.97%; S-22.82%; Found: C-48.80%; H-3.80%; N-9.93%; S-22.70%

EXAMPLE 29

2,7-Dimethyl-4-hydroxy-N-(pyrazinyl)-2H-[1] benzothieno-[2,3-e]-1,2-thiazine-3-carboxamide-1,1-dioxide Prepared analogous to Example 1 from methyl 2,7-dimethyl-4-hydroxy-2H-[1] benzothieno [2,3-e]-1,2-thiazine-3-carboxylate-1,1-dioxide and amino-pyrazine with a yield of 39% of theory.

M.p.: 243°–244° C. (decomp.) after recrystallization from dimethylformamide.

$C_{17}H_{14}N_4O_4S_2$ (402.46): Calc.: C-50.74%; H-3.51%; N-13.92%; S-15.93% Found: C-50.40%; H-3.57%; N-13.62%; S-16.60%

EXAMPLE 30

2,7-Dimethyl-4-hydroxy-N-(3-hydroxy-2pyridyl)-2H-[1]-benzothieno-[2,3-e]-1,2-thiazine-3-carboxamide-1,1-dioxide Prepared analogous to Example 1 from methyl 2,7-dimethyl-4-hydroxy-2H-[1]-benzothieno-[2,3-e]-1,2-thiazine-3-carboxylate-1,1-dioxide and 2-amino-3-hydroxy-pyridine with a yield of 38% of theory.

M.p.: 287°–288° C. (decomp.) after recrystallization from dimethylformamide.

$C_{18}H_{15}N_3O_5S_2$ (417.47): Calc.: C-51.79%; H-3.62%; N-10.02%; S-15.39%; Found: C-51.50%; H-3.68%; N-10.27%; S-14.90%

EXAMPLE 31

2,7-Dimethyl-4-hydroxy-N-(4-methyl-2-pyridyl)-2H-[1]-benzothieno-[2,3-e]-1,2-thiazine-3-carboxamide-1,1-dioxide Prepared analogous to Example 1 from methyl 2,7-dimethyl-4-hydroxy-2H-[1]-benzothieno-[2,3-e]-1,2-thiazine-carboxylate-1,1-dioxide and 2-amino-4-methyl-pyridine with a yield of 36% of theory.

M.p.: 240°–241° C. (decomp.) after recrystallization from 1,2-dichloro-ethane.

$C_{19}H_{17}N_3O_4S_2$ (415.49): Calc.: C-54.93%; H-4.12%; N-10.11%; S-15.43%; Found: C-54.80%; H-4.31%; N-10.05%; S-15.80%

IR (KBr.): OH, NH broad, associated, C=O 1650, $SO_2$ 1150, 1340/cm

UV (ethanol): $\lambda_{max}$ 268, 380–390 nm; after addition of KOH: $\lambda_{max}$ 230, 267, 298, 390–400 nm 1H-NMR (CDCl$_3$+5% CF$_3$CO$_2$D); δ 11.25 (2H-s, exchangeable H); 8.40 (1H-d, J=6.6 Hz, ar.H); 8.27 (1H-d, J=8.6 Hz, ar.H); 7.92 (1H-s, ar.H); 7.75 (1H-s, ar. H); 7.7–7.4 (2H-m; ar.H); 3.15 (3H-s, N—CH$_3$); 2.69 (3H-s, ≧C—CH$_3$) 2.63 (3H-s, ≧C—CH$_3$).

EXAMPLE 32

2,7-Dimethyl-4-hydroxy-N-(6-methyl-2-pyridyl)2H-[1]-benzothieno-[2,3-e]-b 1,2-thiazine-3-carboxamide-1,1-dioxide Prepared analogous to Example 1 from methyl 2,7-dimethyl-4-hydroxy-2H-[1]-benzothieno-[2,3-e]-1,2-thiazine-3-carboxylate-1,1-dioxide and 2-amino-6-methyl-pyridine with a yield of 53% of theory.

M.p.: 235°–236° C. (decomp.) after recrystallization from 1,2-dichloro-ethane.

$C_{19}H_{17}N_3O_4S_2$ (415.49): Calc.: C-54.93%; H-4.12%; N-10.11%; S-15.43%; Found: C-55.10%; H-4.14%; N-10.30%; S-15.97%

EXAMPLE 33

7-Chloro-4-hydroxy-2-methyl-N-(2-pyridyl)-2H-[1]-benzothieno-[2,3-e]-1,2-thiazine-3-carboxamide-1,1-dioxide Prepared analogous to Example 1 from methyl 7-chloro-4-hydroxy-2-methyl-N-(2-pyridyl)-2H-[1]-benzothieno-[2,3-e]-1,2-thiazine-3-carboxylate-1,1-dioxide and 2-amino-pyridine with a yield of 40% of theory.

M.p.: 231°–232° C. (decomp.) after recrystallization from 1,2-dichloroethane.

$C_{17}H_{12}ClN_3O_4S_2$ (421.89): Calc.: C-48.40%; H-2.87%; N-9.96%; S-15.20%; Cl-8.40%; Found: C-48.40%; H-3.34%; N-9.94%; S-14.45%; Cl-8.55%

IR (KBr.): OH, NH broad, associated, C=O 1640, $SO_2$ 1140 1330/cm

UV (ethanol): $\lambda_{max}$ 375 nm ($\epsilon$=0.17); after addition of KOH: $\lambda_{max}$ 298 ($\epsilon$=0.37), 400 nm ($\epsilon$=0.36)

The starting compound was obtained by the following reaction sequence:

(a) Monosodium 2-carboxy-6-chloro-benzo-[b]-thiophene-3-sulfonate

Prepared analogous to Example 1(a) from 3,6-dichlorobenzo[b]-thiophene-2-carboxylic acid chloride (m.p. 132°–133° C.) by hydrolysis with aqueous sodium hydroxide solution and subsequent reaction with sodium hydrogen sulfite in the presence of copper(I)-chloride as a catalyst.

Yield: 68% of theory.

(b) 6-Chloro-2-chlorocarbonyl-benzo-[b]-thiophene-3-sulfonic acid chloride

Prepared analogous to Example 1(b) from monosodium 2-carboxy-6-chloro-benzo-[b]-thiophene-3-sulfonate and phosphorus (V)-chloride in the presence of phosphorus oxide trichloride with a yield of 72% of theory. The product, which crystallized upon cooling, was used in the next step without further purification.

(c) 6-Chloro-2-methoxycarbonyl-benzo-[b]-thiophene-3-sulfonic acid chloride

Prepared analogous to Example 1(c) from 6-chloro-2-chlorocarbonyl-benzo-[b]-thiophene-3-sulfonic acid chloride and methanol in the presence of chloroform.

Yield: 69% of theory.

M.p.: 99°–100° C. after recrystallization from methanol.

$C_{10}H_6Cl_2O_4S_2$ (325.19): Calc.: C-36.94%; H-1.86%; Cl-21.80%; S-19.72%; Found: C-37.15%; H-1.95%; Cl-21.70%; S-19.68

IR ($CH_2Cl_2$): C=O 1740, $SO_2$ 1170, 1375/cm

UV (ethanol): $\lambda_{max}$ 256 ($\epsilon$=0.37), 309 nm ($\epsilon$=0.29); after addition of KOH: $\lambda_{max}$ 247 ($\epsilon$=0.35), 290 nm ($\epsilon$=0.27)

(d) Methyl 6-chloro-3-{[(ethoxycarbonyl-methyl)-methylamino]-sulfonyl}-benzo[b]-thiophene-2-carboxylate Prepared analogous to Example 1(d) from 6-chloro-2-methoxycarbonyl-benzo-[b]-thiophene-3-sulfonic acid chloride, sarcosine methyl ester hydrochloride and tiethylamine with a yield of 61% of theory.

M.p.: 77°–78° C. after recrystallization from methanol.

(e) Methyl 7-chloro-4-hydroxy-2-methyl-2H-[1]-benzothieno[2,3-e]-1,2-thiazine-3-carboxylate-1,1-dioxide Prepared analogous to Example 1(e) from methyl 6-chloro-3-{[(ethoxycarbonyl-methyl)-methylamino]-sulfonyl}-benzo[b]-thiophene-2-carboxylate by reaction with sodium methylene in anhydrous methanol with a yield of 35% of theory.

M.p.: 238°–239° C. (decomp.) after recrystallization from methanol.

$C_{13}H_{10}ClNO_5S_2$ (359.8): Calc.: C-43.40%; H-2.80%; Cl-9.85%; N-3.89%; S-17.82%; Found: C-43.30%; H-2.69%; Cl-10.32%; N-3.89%; S-18.57%

IR ($CH_2Cl_2$): OH, broad, associated; C=O 1660, $SO_2$ 1150, 1350/cm

UV (ethanol): $\lambda_{max}$ 267 ($\epsilon$=0.15), 347 nm ($\epsilon$=0.60); after addition of KOH: $\lambda_{max}$ 233 ($\epsilon$=0.63), 296 ($\epsilon$=0.30) and 382 nm ($\epsilon$=0.30)

1H-NMR (d6-DMSO): δ 8.65 (1H-d, J=2 Hz, ar. H in 6-position); 8.27 (1H-d, J=9 Hz, ar. H in 9-position); 7.84 (1H-d of d, J=2 and 9 Hz, ar. H in 8-position); 4.01 (3H-s, $OCH_3$); 3.11 (3H-s, N—$CH_3$).

EXAMPLE 34

7-Chloro-4-hydroxy-2-methyl-N-(4-methyl-2-pyridyl)-2H-[1]-benzothieno-[2,3-e]-1,2-thiazine-3-carboxyamide-1,1-dioxide Prepared analogous to Example 1 from methyl 7-chloro-4-hydroxy-2-methyl-2H-[1]-benzothieno-[2,3-e]-1,2-thiazine-3-carboxylate-1,1-dioxide and 2-amino-4-methyl-pyridine with a yield of 50% of theory.

M.p.: 232°–233° C. (decomp.) after recrystallization from 1,2-dichloro ethane.

$C_{18}H_{14}ClN_3O_4S_2$ (435.91): Calc.: C-49.60%; H-3.24%; N-9.64%; S-14.71%; Cl-8.13%; Found: C-49.60%; H-3.35%; N-9.72%; S-14.68%; Cl-8.67%

IR (KBr.): OH, NH broad, associated, c=O 1650, $SO_2$ 1150, 1340/cm

UV (ethanol): $\lambda_{max}$ 270 ($\epsilon$=0.30), 300–330 ($\epsilon$=0.30), 395 nm ($\epsilon$=0.4); after addition of KOH: $\lambda_{max}$ 298 ($\epsilon$=0.41), 400 nm ($\epsilon$=0.4).

1H-NMR (d6-DMSO): δ 1470 (1H-s, exchangeable H); 8.54 (1H-d, J=2 Hz, ar. H in 6-position); 8.32 (1H-d, J=6.6 Hz, ar.H in 6'-position); 8.18 (1H-J=9 Hz, ar. H in 9-position); 7.9–7.6 (2H-m; ar. H in 8- and 3'-position9; 7.37 (1H-d of d, J=6.6 and 1.5 Hz, ar. H in 5'-position); 1-exchangeable H at about 3.5 to 5.0; 3.05 (3H-s, N—$CH_3$); 2.58 (3H-s; ≧C—$CH_3$).

EXAMPLE 35

7-Chloro-4-hydroxy-2-methyl-N-(6-methyl-2-pyridyl)-2H-[1]-benzothieno-[2,3-e]-1,2-thiazine-3-carboxamide-1,1-dioxide Prepared analogous to Example 1 from methyl 7-chloro-4-hydroxy-2-methyl-2H-[1]-benzothieno-2,3-e]-1,2-thiazine-3-carboxylate-1,1-dioxide and 2-amino-6-methyl pyridine with a yield of 50% of theory.

M.p.: 245°–246° C. (decomp.) after recrystallization from dimethyl formamide/methanol (4:1).

IR (KBr.): associated N-H or OH 3600 to 2300, C=O 1640, amide-II 1560, —$SO_2N$— 1140, 1330/cm, UV (ethanol): $\lambda_{max}$ (neutral) 255–275 (E=0.14); 375–380 (E=0.22)nm; $\lambda_{max}$ (alkaline) 300 (E=0.38); 404 (E=0.35)nm shoulder at 245 nm (E=0.4)

Concentration: 60 μg/ml; thickness of layer: 0.2 cm)

$^1$H-NMR (CDCl$_3$+10% CF$_3$CO$_2$$^2$H; 80 MHz): δ 13.0–12.3 (2H, broad, exchangeable protons); 8.55–8.0 (4H-m; ar.H); 7.8–7.4 (2H-m; ar.H); 3.08 (3H-s; N—CH$_3$); 2.83 (3H-s; C—CH$_3$).

$C_{18}H_{14}ClN_3O_4S_2$ (435.91): Calc.: C-49.60%; H-3.24%; N-9.64%; S-14.71%; Cl-8.13%; Found: C-49.20%; H-3.395; N-9.69%; S-14.78%; C-8.14%

EXAMPLE 36

7-Chloro-4-hydroxy-2-methyl-N-(2-thiazolyl)-2H-[1] benzothieno [2,3-e]-1,2-thiazine-3-carboxamide-1,1-dioxide Prepared analogous to Example 1 from methyl 7-chloro-4-hydroxy-2-methyl-2H-[1] benzothieno [2,3-e]-1,2-thiazine-3-carboxylate-1,1-dioxide and 2-amino-thiazole with a yield of 56% of theory.

M.p.: 259°–260° C. (decomp.) after recrystallization from dimethyl formamide.

$C_{15}H_{10}N_3O_4S_3$ (427.91): Calc.: C-42.10%; H-2.36%; N-9.82%; S-22.48%; Cl-8.28%; Found: C-42.35%; H-2.48%; N-9.86%; S-22.35%; Cl-8.38%

EXAMPLE 37

7-Chloro-4-hydroxy-2-methyl-N-(4-methyl-2-thiazolyl)-2H-[1] benzothieno [2,3-e]-1,2-thiazine-3-carboxamide-1,1-dioxide Prepared analogous to Example 1 from methyl 7-chloro-4-hydroxy-2-methyl-2H-[1] benzothieno [2,3-e]-1,2-thiazine-3-carboxylate-1,1-dioxide and 2-amino-4-methyl-thiazole with a yield of 36% of theory.

M.p.: 233°–234° C. (decomp.) after recrystallization from 1,2-dichloro-ethane.

$C_{16}H_{12}ClN_3O_4S_3$ (441.94): Calc.: C-43.48%; H-2.74%; N-9.51%; S-21.77%; Cl-8.02%; Found: C-43.60%; H-2.83%; N-9.45%; S-21.50%; Cl-8.10%

EXAMPLE 38

7-Chloro-4-hydroxy-2-methyl-N-(5-methyl-2-thiazolyl)-2H-[1] benzothieno [2,3-e]-1,2-thiazine-3-carboxamide-1,1-dioxide Prepared analogous to Example 1 from methyl 7-chloro-4-hydroxy-2-methyl-2H-[1] benzothieno [2,3-e]-1,2-thiazine-3-carboxylate-1,1-dioxide and 2-amino-5-methyl-thiazole with a yield of 42% of theory.

M.p.: 261°–262° C. (decomp.) after recrystallization from dimethylformamide.

$C_{16}H_{12}ClN_3O_4S_3$ (441.94): Calc.: C-43.48%; H-2.74%; N-9.51%; S-21.77%; Cl-8.02%; Found: C-43.60%; H-2.78%; N-9.63%; S-21.40%; Cl-8.35%

EXAMPLE 39

7-Chloro-4-hydroxy-2-methyl-N-(pyrazinyl)-2H-[1] benzothieno-[2,3-e]-1,2-thiazine-3-carboxamide-1,1-dioxide Prepared analogous to Example 1 from methyl 7-chloro-4-hydroxy-2-methyl-2H-[1] benzothieno [2,3-e]-1,2-thiazine-3-carboxylate-1,1-dioxide and amino-pyrazine with a yield of 70% of theory.

M.p.: 247°–248° C. (decomp.) after recrystallization from dimethylformamide.

$C_{16}H_{11}ClN_4O_4S_2$ (422.87): Calc.: C-45.45%; H-2.62%; N-13.25%; S-15.16%; Cl-8.38%; Found: C-45.20%; H-2.66%; N-12.95%; S-15.33%; Cl-8.48%

The compounds of the present invention, that is, those embraced by formula I above and non-toxic, pharmacologically acceptable salts formed with inorganic or organic bases, have useful pharmacodynamic properties. More particularly, they exhibit analgesic, antipyretic, antiphlogistic and/or antithrombotic activities in warm-blooded animals.

The antithrombotic and antiphlogistic properties and the toxicities of the compounds of this invention were determined and compared to those of known compounds by the test methods described below, and the results of these tests for a few representative species and the prior art compounds are shown in the tables, where A = 4-Hydroxy-2-methyl-N-(2-thiazolyl)-2H-[1] benzothieno-[2,3-e]-1,2-thiazine-3-carboxamide-1,1-dioxide, B = 4-Hydroxy-2-methyl-N-(6-methyl-2-pyridyl)-2H-[1] benzothieno [2,3-e]-1,2-thiazine-3-carboxamide-1,1-dioxide, C = 4-Hydroxy-2-methyl-N-(4-methyl-2-thiazolyl)-2H-[1] benzothieno [2,3-e]-1,2-thiazine-3-carboxamide-1,1-dioxide, D = 4-Hydroxy-2-methyl-N-(4-methyl-2-pyridyl)-2H-[1]-benzothieno-[2,3-e]-1,2-thiazine-3-carboxamide-1,1-dioxide, E = 2,7-Dimethyl-4-hydroxy-N-(4-methyl-2-pyridyl)-2H-[1]-benzothieno [2,3-e]-1,2-thiazine-3-carboxamide-1,1-dioxide, F = 2,7-Dimethyl-4-hydroxy-N-(6-methyl-2-pyridyl)-2H-[1]-benzothieno [2,3-e]-1,2-thiazine-3-carboxamide-1,1-dioxide, G = 7-Chloro-4-hydroxy-2-methyl-N-(4-methyl-2-pyridyl)-2H-[1]-benzothieno [2,3-e]-1,2-thiazine-3-carboxamide-1,1-dioxide, H = 7-Chloro-4-hydroxy-2-methyl-N-(6-methyl-2-pyridyl)-2H-[1] benzothieno [2,3-e]-1,2-thiazine-3-carboxamide-1,1-dioxide, I = N-(2-Benzothiazolyl)-4-hydroxy-2-methyl-2H-[1] benzothieno [2,3-e]-1,2-thiazine-3-carboxamide-1,1-dioxide, J = N-(5-Chloro-2-thiazolyl)-4-hydroxy-2-methyl-2H-[1] benzothieno [2,3-e]-1,2-thiazine-3-carboxamide-1,1-dioxide, K = N-(4,5-Dimethyl-2-thiazolyl)-4-hydroxy-2-methyl-2H-[1]-benzothieno [2,3-e]-1,2-thiazine-3-carboxamide-1,1-dioxide, V = Acetylsalicyclic acid, and W = Sudoxicam.

1. Inhibition of blood-platelet aggregation

The thrombocyte aggregation was measured according to the method of BORN and CROSS (J. Physiol. 170, 397, [1967]) in platelet-rich plasma of healthy test persons. The decrease in the optical density of platelet suspensions was measured photometrically and recorded after the addition of collagen.

From the angle of inclination of the density curve the velocity of aggregation was estimated. The optical density was taken as the point on the curve where the most light was transmitted.

The doses of collagen were chosen so as to be sufficient to produce irreversible aggregation.

The figures indicated refer to the optical density and give the change in the transmission of light in percent (=% decrease in aggregation) under the influence of the test compound in comparison to the control.

Commercial collagen sold by Hormonchemie, Munich, Germany, was used.

The following table shows the results obtained from this test:

| Compound | Concentration mol/liter | Percentage change in light permeability of plasma (Born test) |
|---|---|---|
| A | $10^{-5}$ | 94 |
|   | $10^{-6}$ | 73 |
|   | $10^{-7}$ | 14 |
| B | $4.10^{-6}$ | 100 |
|   | $4.10^{-7}$ | 71 |
| C | $10^{-5}$ | 93 |
|   | $10^{-6}$ | 57 |
| D | $2.10^{-5}$ | 88 |
|   | $2.10^{-6}$ | 60 |
|   | $2.10^{-7}$ | 19 |
| E | $2.10^{-5}$ | 72 |
|   | $2.10^{-6}$ | 34 |
| F | $2.10^{-5}$ | 90 |
|   | $2.10^{-6}$ | 77 |
|   | $2.10^{-7}$ | 30 |
| G | $2.10^{-5}$ | 66 |
|   | $2.10^{-6}$ | 33 |
| H | $2.10^{-5}$ | 89 |
|   | $2.10^{-6}$ | 88 |
|   | $2.10^{-7}$ | 33 |
| V | $3.10^{-5}$ | 45 |
|   | $10^{-5}$ | 13 |

2. Anti-inflammatory activity

The anti-inflammatory activity [see Vane in Nature New Biology 231, 232, (1971)], the analgesic activity [see Ferreira in Nature New Biology 240, 200 (1972)] and also the antipyretic activity [see Flower and Vane in Nature New Biology 240, 410 (1972)] of the nonsteroidal antiphlogistics are predicated by the mechanism of inhibition of the prostaglandin biosynthesis.

Therefore, the anti-inflammatory activity was determined as the activity against the prostaglandin synthetases:

Method:

The determination of the rate of prostaglandin biosynthesis was carried out radiochemically by means of a modification of the method of WHITE and GLASSMAN [Prostaglandins, 7, 123 (1974)]. The prostaglandin synthetases were isolated as a microsomal extract from bovine seminal vesicles according to FLOWER et al. [Prostaglandins 4, 325 (1973)].

$^{14}$C-arachidonic acid served as the substrate. The prostaglandins biosynthetisized therefrom were separated chromatographically from the $^{14}$C-arachidonic acid, and the remaining substrate and product were measured radiochemically.

From the amount of prostaglandins eluted after the action of different concentrations of the test compound (measured in dpm, based on 20,000 dpm of eluted prostaglandin+arachidonic acid, an $EC_{50}$ was calculated by linear regression analysis according to LINDER (Statistische Methoden, 4th edition, pp. 148-162, Birkhäuser, Basel 1964) as that end concentration in the test system which led to a 50% decrease in the amount of prostaglandins over the control batches without the test compound.

The results of this test are shown in the following table:

| Compound | $n_1$ | $n_2$ | DMSO* % | $EC_{50}$ in mol |
|---|---|---|---|---|
| A | 3 | 6 | 2 | $3.9 \times 10^{-8}$ |
| C | 4 | 6 | 2 | $2.1 \times 10^{-8}$ |
| K | 5 | 5-6 | 10 | $2.5 \times 10^{-7}$ |
| I | 5 | 6 | 2 | $2.2 \times 10^{-8}$ |
| J | 5 | 6 | 2 | $4.7 \times 10^{-8}$ |
| W | 5 | 6 | 2 | $7.0 \times 10^{-6}$ |

$n_1$ = number of the tested concentrations
$n_2$ = number of the samples/concentration
* = concentration of the solution promoter DMSO in the end composition.

3. Acute toxicity

The acute toxicity was determined in rats of both sexes (1:1) with a body weight of 120-150 gm. The test compound was perorally administered as a suspension in 1% methyl-cellulose (1 ml/100gm animal) by means of an esophageal sound. The animals were observed for 24 hours after treatment.

The following table shows the results obtained:

| Substance | Toxicity |
|---|---|
| A | >100 mg/kg p.o. (0 out of 10 animals died) |
| C | >100 mg/kg p.o. (0 out of 10 animals died) |
| K | >100 mg/kg p.o. (0 out of 10 animals died) |
| I | >100 mg/kg p.o. (0 out of 10 animals died) |
| J | >100 mg/kg p.o. (0 out of 10 animals died) |

Based on their pharmacological properties, the novel compounds of the formula I and their non-toxic salts formed with inorganic or organic bases are particularly suitable for the treatment of inflammations of different origins, such as post-traumatic inflammations and swellings, non-traumatic inflammations of the apparatus of locomotion (incl. rheumatic inflammations), inflammations and swellings after operations, inflammations of the adnexal organs, of the blood and lymphatic system, and/or for the prophylaxis of arterial thromboembolisms and arterial vessel diseases.

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions suspensions, emulsions, syrups, suppositories and the like. One effective dosage unit of the compounds according to the present invention is from 0.16 to 4.2 mgm/kg body weight, preferably 0.42 to 1.7 mgm/kg body weight. The daily dose is 0.42 to 8.3 mgm/kg, preferably 0.83 to 4.2 mgm/kg.

The following examples illustrate a few pharmaceutical dosage unit compositions comprising a compound of the present invention as an active ingredient and represent the best modes contemplated of using the invention. The parts are parts by weight unless otherwise specified.

EXAMPLE 40

Tablets

The tablet composition is compounded from the following ingredients:

| | | |
|---|---|---|
| 4-Hydroxy-2-methyl-N-(2-pyridyl)-2H-[1]benzothieno[2,3-e]-1,2-thiazine-3-carboxamide-1,1-dioxide | | 50.0 parts |
| Corn starch | | 97.0 parts |
| Polyvinylpyrrolidone | | 175.0 parts |
| Magnesium stearate | | 3.0 parts |
| | Total: | 325.0 parts |

Preparation:

The active ingredient and the corn starch are intimately admixed with each other, the mixture is uniformly moistened with an aqueous 14% solution of the polyvinylpyrrolidone, the moist mass is granulated by passing it through a 1.5 mm mesh screen, and the granulate is dried at 45° C. and again passed through the screen. The dry granulate is admixed with the magnesium stearate, and the composition is compressed into 325 mgm-tablets. Each tablet is an oral dosage unit composition containing 50 mgm of the active ingredient.

EXAMPLE 41

Coated Pills

The pill core composition is compounded from the following ingredients:

| | | |
|---|---|---|
| 4-Hydroxy-2-methyl-N-(2-pyridyl)-2-H-[1] benzothieno [2,3-e]-1,2-thiazine-3-carboxamide-1,1-dioxide | | 50.0 parts |
| Corn startch | | 245.0 parts |
| Gelatin | | 8.0 parts |
| Talcum | | 18.0 parts |
| Magnesium stearate | | 4.0 parts |
| | Total: | 325.0 parts |

Preparation:

The active ingredient and the corn starch are intimately admixed with each other, the mixture is uniformly moistened with an aqueous 10% solution of the gelatin, the moist mass is granulated by passing it through a 1.5 mm-mesh screen, and the granulate is dried at 45° C. and again passed through the screen. The dry granulate is admixed with the talcum and the magnesium stearate, and the composition is compressed into 325 mgm-pill cores which are subsequently coated with a thin shell consisting essentially of a mixture of talcum and sugar, and polished with beeswax. Each coated pill is an oral dosage unit composition containing 50 mgm of the active ingredient.

EXAMPLE 42

Gelatin Capsules

The capsule filler composition is compounded from the following ingredients:

| | | |
|---|---|---|
| 4-Hydroxy-2-methyl-N-(4-methyl-2-pyridyl)-2H-[1] benzothieno-[2,3-e]-1,2-thiazine-3-carboxamide-1,1-dioxide | | 50.0 parts |
| Corn starch | | 365.0 parts |
| Colloidal silicic acid | | 6.0 parts |
| Magnesium stearate | | 4.0 parts |
| | Total: | 425.0 parts |

Preparation:

The ingredients are intimately admixed with each other, and 425 mgm portions of the resulting composition are filled into No. 1 hard gelatin capsules. Each capsule is an oral dosage unit containing 50 mgm of the active ingredient.

EXAMPLE 43

Suppositories

The suppository composition is compounded from the following ingredients:

| | | |
|---|---|---|
| 4-Hydroxy-2-methyl-N-(4-methyl-2-pyridyl)-2H-[1] benzothieno-[2,3-e]-1,2-thiazine-3-carboxamide-1,1-dioxide | | 50.0 parts |
| Suppository base (e.g. cocoa butter) | | 1725.0 parts |
| | Total: | 1775.0 parts |

Preparation:

The finely pulverized active ingredient is stirred with the aid of an immersion homogenizer into the suppository base which had been melted and cooled to 40° C. 1775 mgm-Portions of the resulting composition are poured at 38° C. into cooled suppository molds and allowed to harden therein. Each suppository is a rectal dosage unit composition containing 50 mgm of the active ingredient.

Any one of the other compounds embraced by formula I or a non-toxic, pharmacologically acceptable salt thereof may be substituted for the particular active ingredient in Examples 40 through 43. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

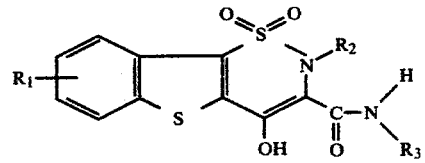

wherein R$_1$ is hydrogen, halogen or alkyl of 1 to 3 carbon atoms;

R$_2$ is hydrogen or alkyl of 1 to 3 carbon atoms; and

R$_3$ is phenyl, naphthyl, pyridyl, pyrimidyl, pyrazinyl, pyridazinyl, oxazolyl, isooxazolyl, thiazolyl, isothiazolyl, benzothiazolyl, 4,5,6,7-tetrahydro-benzothiazolyl, cyclopentathiazolyl or 1,3,4-thiadiazolyl, where each of these substituents may be substituted with one or two alkyls of 1 to 6 carbon atoms, halogen, hydroxyl, trifluoromethyl, halophenyl or alkoxy of 1 to 3 carbon atoms;

or a non-toxic, pharmacologically acceptable salt thereof formed with an inorganic or organic base.

2. A compound of claim 1, where $R_1$ is hydrogen, chlorine or methyl;

$R_2$ is methyl; and $R_3$ is phenyl, chloro-phenyl, pyridyl, chloropyridyl, hydroxy-pyridyl, methyl-pyridyl, thiazolyl, mono- or di-(alkyl of 1 to 4 carbon atoms)-thiazolyl, chloro-thiazolyl, trifluoromethyl-thiazolyl, chlorophenyl-thiazolyl, benzo-thiazolyl, 5,6-dimethyl-benzothiazolyl, 4,5,6,7-tetrahydro-benzothiazolyl, 5,6-dihydro-4H-cyclopentathiazolyl, 5-methyl-isoxazolyl, pyrimidyl or pyrazinyl;

or a non-toxic, pharmacologically acceptable salt thereof formed with an inorganic or organic base.

3. A compound of claim 1
where $R_1$ is in 7-position and has the meanings defined in claim 2, $R_2$ has the meanings defined in claim 2, and $R_3$ is thiazolyl-(2), Pyridyl-(2), 6-methylpyridyl-(2), 4-methyl-pyridyl-(2), 5-chlorothiazolyl-(2), 4-methyl-thiazolyl-(2) or 4,5-dimethyl-thiazolyl-(2);

or a non-toxic, pharmacologically acceptable salt thereof formed with an inorganic or organic base.

4. A compound of claim 1, which is 4-hydroxy-2-methyl-N-(2-pyridyl)-2H-[1] benzothieno [2,3-e]-1,2-thiazine-3-carboxamide-1,1-dioxide or a non-toxic, pharmacologically acceptable salt thereof formed with an inorganic or organic base.

5. A compound of claim 1, which is 4-hydroxy-2-methyl-N-(4-methyl-2-pyridyl)-2H-[1] benzothieno [2,3-e]-1,2-thiazine-3-carboxamide-1,1-dioxide or a non-toxic, pharmacologically acceptable salt thereof formed with an inorganic or organic base.

6. A compound of claim 1, which is 7-chloro-4-hydroxy-2-methyl-N-(6-methyl-2-pyridyl)-2H-[1]-benzothieno [2,3-e]-1,2-thiazine-3-carboxamide-1,1-dioxide or a non-toxic, pharmacologically acceptable salt thereof formed with an inorganic or organic base.

7. A compound of claim 1, which is 2,7-dimethyl-4-hydroxy-N-(4-methyl-2-pyridyl)-2H-[1] benzothieno [2,3-e]-1,2-thiazine-3-carboxamide-1,1-dioxide or a non-toxic, pharmacologically acceptable salt thereof formed with an inorganic or organic base.

8. An antithrombotic or antiphlogistic pharmaceutical dosage unit composition consisting essentially of an inert pharmaceutical carrier and an effective antithrombotic or antiphlogistic amount of a compound of claim 1.

9. The method of preventing or relieving thrombosis or counteracting inflammation and fever in a warm-blooded animal in need thereof, which comprises per-orally, parenterally or rectally administering to said animal an effective antithrombotic or antiphlogistic amount of a compound of claim 1.

* * * * *

UNITED STATES PATENT AND TRADEMARK OFFICE
CERTIFICATE OF CORRECTION

PATENT NO. : 4,259,336                    Page 1 of 2
DATED      : March 31, 1981
INVENTOR(S): WOLFHARD ENGEL ET AL.

It is certified that error appears in the above—identified patent and that said Letters Patent is hereby corrected as shown below:

Column 6, line 13: "3-}[(ethoxy" shoul read -- 3-{[(ethoxy --.

Column 7, line 39: "FOund" should read -- Found --.

Column 8, line 17: "ixoxazolyl" should read -- isoxazolyl --.

Column 9, line 22: "[2,3-3]" should read -- [2,3-e] --.

line 47: "2methyl" should read -- 2-methyl --.

Column 12, line 66: "methox" should read -- methoxy --.

line 67: "ycarbonyl" should read -- carbonyl --.

Column 13, line 30: "-2,3-e]" should read -- -[2,3-e] -- line 59: "Dimethyl-2-hydroxy" should read
         -- Dimethyl-4-hydroxy --.

Column 14, line 21: "2pyridyl" should read -- 2-pyridyl --.

Column 16, line 2: "tiethylamine" should read
         -- triethylamine --.

line 31: "carboxya-" should read -- carboxamide- --.

line 50: "(1H-J=9 Hz," should read
         -- (1H-d, J=9Hz, -- line 52: Please delete "9".

UNITED STATES PATENT AND TRADEMARK OFFICE
CERTIFICATE OF CORRECTION

PATENT NO. : 4,259,336

DATED : March 31, 1981

INVENTOR(S) : WOLFHARD ENGEL ET AL.

It is certified that error appears in the above—identified patent and that said Letters Patent is hereby corrected as shown below:

Column 16, line 62: "benzothieno-2,3-e] should read -- benzothieno[2,3-e] --.

Column 17, line 11: "H-3.395" should read -- H-3.39% --.

line 11: "C-8.14%" should read -- Cl-8.14% --.

Signed and Sealed this

First Day of September 1981

[SEAL]

Attest:

Attesting Officer

GERALD J. MOSSINGHOFF

Commissioner of Patents and Trademarks